United States Patent [19]

Quillfeldt et al.

[11] Patent Number: 4,711,572
[45] Date of Patent: Dec. 8, 1987

[54] METHOD AND ARRANGEMENT FOR MULTIELEMENT ANALYSE

[75] Inventors: Winfried Quillfeldt; Bernd Naumann, both of Jena-Lobeda; Helmut Becker-Ross, Berlin, all of German Democratic Rep.

[73] Assignee: Jenoptik Jena GmbH, Jena, German Democratic Rep.

[21] Appl. No.: 680,220

[22] Filed: Dec. 10, 1984

[30] Foreign Application Priority Data

Dec. 1, 1983 [DD] German Democratic Rep. ............ 2573606
Mar. 1, 1984 [DD] German Democratic Rep. ............ 2604567

[51] Int. Cl.$^4$ ............................................. G01J 3/443
[52] U.S. Cl. .................................... 356/311; 356/316; 356/326
[58] Field of Search ............... 356/310, 311, 315, 316, 356/326, 328, 329

[56] References Cited

U.S. PATENT DOCUMENTS

| 3,880,523 | 4/1975 | Thomas | 356/328 |
| 4,320,972 | 3/1982 | Strasheim et al. | 356/328 |
| 4,326,802 | 4/1982 | Smith, Jr. et al. | 356/334 |
| 4,346,998 | 8/1982 | Franklin | 356/316 |
| 4,375,919 | 3/1983 | Busch | 356/328 |
| 4,391,523 | 7/1983 | Hildebrand et al. | 356/328 |

FOREIGN PATENT DOCUMENTS

| 3304110 | 8/1984 | Fed. Rep. of Germany | 356/319 |
| 0137226 | 10/1981 | Japan | 356/326 |

Primary Examiner—F. L. Evans
Assistant Examiner—Joel L. Harringa
Attorney, Agent, or Firm—Jordan and Hamburg

[57] ABSTRACT

The invention relates to an arrangement and method for multielement analyse of chemical elements in which light cables are used to transmit spectral lines or bands produced by an optical dispersion means from a sample material radiation to an array of photodetectors. The light cable end-portions are inserted as many as required for a definite analyzing program into holes of a plug-in unit and are associated via a mask to definite photodetectors. The plug-in unit is displaceable relative to the mask so that the spectral informations from definite light cables associated to definite spectral lines or bands are evaluated in groups which require similar or equal excitation conditions. The latter are adjustable by respective means.

7 Claims, 1 Drawing Figure

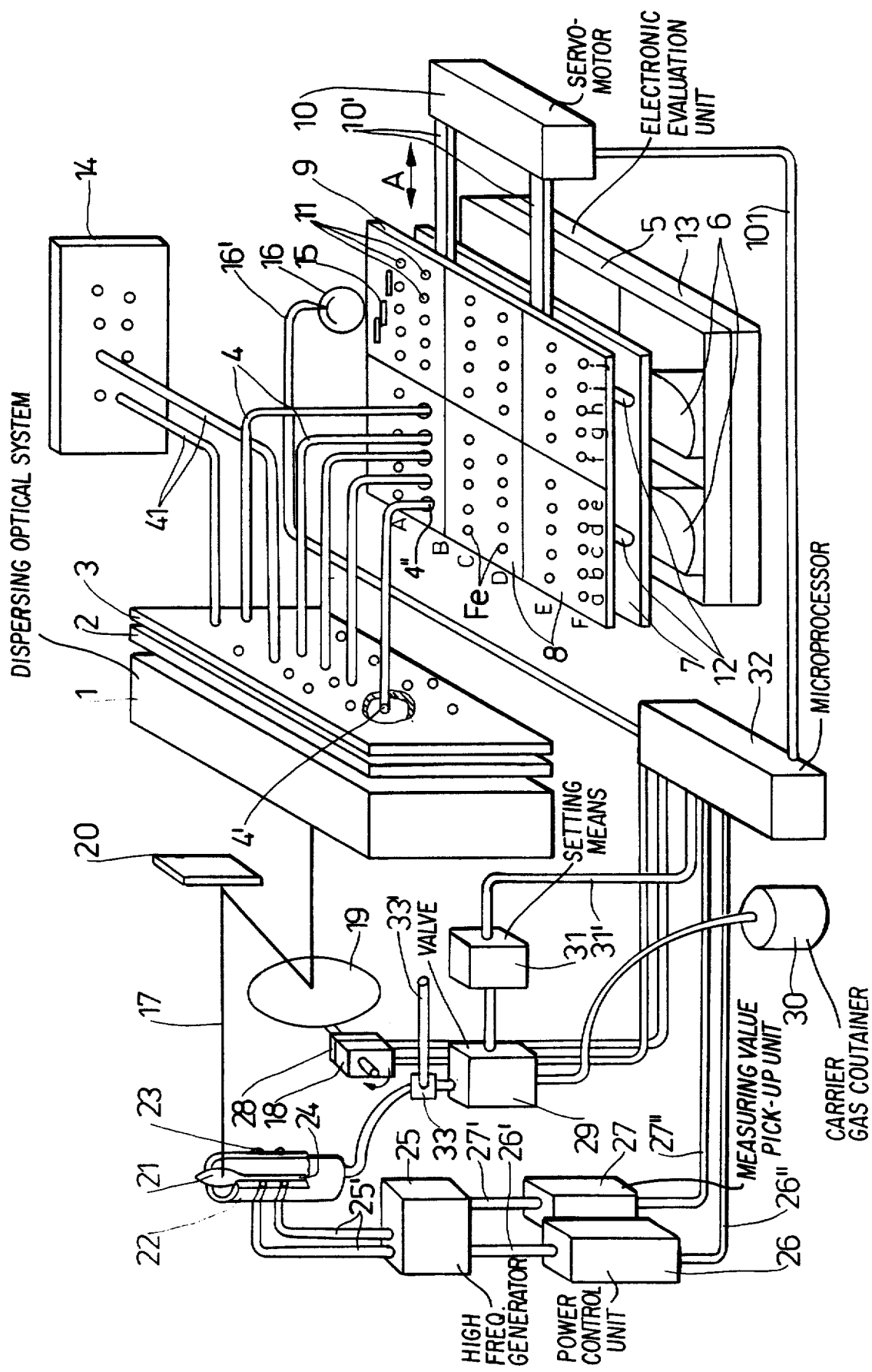

METHOD AND ARRANGEMENT FOR MULTIELEMENT ANALYSE

The invention relates to a method and arrangement for a multielement analysis, particularly for use in emission spectral analysis and in multi-channel atomic absorption analysis or in spectral photometry wherein spectral lines or bands are selected from an entire spectrum.

Apparatus for multielement emission analysis generally comprise an arrangement for thermal or athermal excitation of the chemical elements containes in a sample material, said arrangement represents the radiation source or the excitation source, an imaging optical system, a dispersion optical system, an optical system for selecting spectral lines, photoelectrical detectors and an electronic detection system.

The selected light is transmitted to the detectors by optical members such as prisms, reflectors and light cables.

The known apparatus have the disadvantage that either as many detectors have to be provided as elements are contained in the sample material to be analysed, or only the spectral lines typical of a definite sample quality are selected from the great number of feasible spectral lines by optical means which are non-displaceably arranged.

In the first case a great number of detectors and electronic detection channels is provided which is not required in each sample analyse. In the second case only a few detectors are used, however, for each different sample material a respective optical system is required for selection which renders the apparatus expensive.

The excitation of the spectral lines of the individual elements depends on the temperature or on the electron density. Since the excitation volume of a radiation source is spatially limited by a cooler ambiance each radiation source exhibits a more or less strong heterogeneity. Therefore, spectral lines of different excitation energies are optimally excited in different loci of the radiation source. The same effect prevails in the case of heteroeneous electron densities.

These features are particularly striking when an ICP (inductively coupled plasma) is used as an excitation source. Then the optimum excitation ranges for the individual chemical elements can be remote from one another by up to 20 mm.

Sequential operation spectrometers having ICP excitation generally known as plasma spectrometers therefore very often have a device for imaging the excitation source into a dispersing optical system (DOS). The device permits to select the most suitable locus (observation height) in the plasma for the spectral lines, programed and controlled by a microprocessor according to said spectral lines set by the DOS.

Simultaneously operating spectrometers do not have such devices. They are capable to detect one point in the excitation source and therefore do not obtain the detection efficiency of the sequential operation spectrometers. When only a small amount of sample material is at one's disposal - so that a pulsed emission of the excitation source by sample injection or laser atomization is required (or that the sample material is not continuously atomized as in the event of flash atomization or that very short sampling times for a large number of elements are necessary) a sequential detection of optimal excitation zones has a negative effect.

Apart from the dependence of the spectral line emission on the location of the image there are still other dependencies which concern individual spectral lines, such as the intensity of the emission on the electric power capacity of the excitation source and on the carrier gas flow for the sample material when sprayed as an aerosol.

In these cases there can prevail a direct or indirect proportionality or a maximum can be passed.

The known sequentially operating spectrometers only for a part take into consideration the dependence on the electrical power capacity in that the latter is programed for each individual spectral line.

Therefore, it is feasible with ICP sequentially operating spectrometers when a definite spectral line is investigated to image the observation height and, at the same time, to set the most suitable electrical power for this spectral line.

It is disadvantageous that the optimization of the observation height, of the electrical power, and of the carrier gas flow has to be carried out for each spectral line individually, therefore the sequentially operating spectrometers require a very constant excitation source the emission of which is stable for a few minutes.

Additionally, the entire measuring time considerably increases.

As concerns the known simultaneously operating spectrometers so-called compromise conditions have to be entered in setting the measuring parameters, which results in the fact that not the best analytical efficiency is attained.

It is an object of the present invention to obviate the above disadvantages.

It is a further object of the present invention to provide a measuring arrangement for a simultaneous detection of a plurality of spectral lines or bands which increases the analytic efficiency.

It is still a further object of the present invention to provide a measuring arrangement which permits a considerably short measuring time for a simultaneous investigation of sample materials at a reduction of costs.

It is still another object of the invention to provide a measuring arrangement for analyzing sample materials which permits the selective setting of the measuring parameters observation height, power efficiency and carrier gas flow for a simultaneous detection of a plurality of spectral lines or bands with each detector under use of only one dispersing optical member.

These and other objects are realised in an arrangement for multielement analysis of sample materials comprising a plurality of light exit slits which serve to select a number of spectral lines from out of an entire spectrum, each of said light exit slits is associated to at least one light cable. The light cables are connectable via their end portions to a plug-in unit which is divided into definite sections. Each of the sections is associated to a detector means which, in turn, is connected to an evaluation electronic unit. According to the invention a mask is inserted between the plug-in unit and the detector means, the mask is provided with at least one slit which optically connects each of the detector means to definite portions of the sections. Means are provided to displace the plug-in unit relative to the mask in a plane which is substantially in parallel to both, the plug-in unit and to a plane defined by the detecting faces of the detectors. The plug-in unit is provided with code marks which define the optical association of the plug-in positions of the light cables in the plug-in unit relative to the detectors. A microprocessor is provided which is connected to setting means for setting at least one measuring parameter and to a signal detector which is associated to the code marks.

A preselected value for at least one measuring parameter is stored in the microprocessor for each association.

Each of said sections contains at least one line of plug-in holes for respective light-cables.

At least one of the plug-in holes of each section is optically connected to one of the detectors via the mask. It is a further object of the present invention to provide a method for multielement analysis wherein the spectral lines or bands from a radiation source are directed upon the detectors via light cables.

The light cables which transmit spectral lines or bands which require identical or similar measuring parameters are collected to form groups which are subsequently optically associated to respective detectors.

Thus, it is feasible to optimize the measuring parameters to be set for an entire unit or group of spectral lines which increases the measuring efficiency and reduces the measuring time.

According to the inventive arrangement as many spectral lines can be evaluated at one time as there are detectors provided.

Since the light cables which are associated to the exit slits are selectively connectable to the different sections of the plug-in unit the number of detectable spectral lines increases due to the stepping displacement of the plug-in unit relative to the mask.

Thereby the plug-in holes gradually pass the openings in the mask. The number of spectral lines to be detected is equal the product of the number of detectors and the feasible displaced positions which correspond to the number of plug-in holes arranged in the sections. In order to increase the intensity of the spectral light of an element to be analyzed further lines of plug-in holes are provided in the sections of the plug-in unit which are parallel to the first line, in which each hole in the first line is adjacent to a hole in the further lines.

These adjacent holes permit insertion of further light cables which are associated to other spectral lines of a same element to be analyzed. In this manner one detector at one time detects the spectral light from several spectral lines of one element to be analyzed, which light passes one opening in the mask. The opening is embodied to optically and simultaneously connect the adjacent plug-in holes belonging to different lines of plug-in holes to one detector.

Advantageously, the displacement of the plug-in unit relative to the mask is combined with an amplification variation of the individual detecting channels as well as with a variation of the electronic signal integration in the evaluation electronic unit connected to the detectors.

In order that the invention may be more readily understood reference is made to the accompanying drawing which illustrates diagrammatrically and by way of example one embodiment thereof and where the FIGURE is a schematical and perspective view of a multielement analyzing arrangement.

A dispersing optical system or means 1, for example, a diffraction grating spectrometer, is followed in the direction of light propagation of a radiation 17 by a mask 2 comprising an array of exit slits (only the mask 2 visible) which is coupled to a block 3 including an array of light entry faces 4' of light cables 4, only a part thereof designated. Each of the light entry faces 4' is associated to a respectively positioned exit slit (not visible) of the array of exit slits (2). The one end portions of the light cables 4 are secured in any suitable manner to the block 3. The light entry faces 4' of the light cables 4 are in a plane with the surface of the block 3 which is in opposition to the mask 2. The exit slits of the mask 2 are arranged to enable the selection of spectral lines, that is, the individual exit slits are associated to respective spectral lines on the output face (not visible) of the grating 1.

A plug-in unit 9, a mask 7 and a detector unit 5 are arranged subsequently in parallel planes to one another at a small relative distance. The plug-in unit 9 is provided with a plurality of holes 11 which permit insertion of the other end portions of the light cables 4 thereinto so that the light exit faces 4" of the light cables 4 (when inserted) are in opposition to the mask 7. The plug-in unit 9 is a substantially plane rectangular plate which is subdivided into a plurality (six in the present embodiment) of sections 8 of equal size and geometry. Means 10' and a servo-motor 10 are provided to displace the plug-in unit 9 in parallel to the plane of the mask 7 in directions which are indicated by the double arrow A.

Each of the sections 8 contains two parallel lines of plug-in holes 11 which are symmetrically to one another in two coordinate directions. The plug-in holes 11 are, hence, arranged in six parallel lines designated by the capital letters A, B, C, D, E, F and in ten columns designated by the minuscules a . . . j. The detector unit 5 comprises a plurality of light detection means 6 (in the present embodiment six light detectors) which optically cover at least one hole 11 in the corresponding overlying plug-in unit 9. The mask 7 has six slits 12 which are arranged along two parallel lines which, in turn, are at right angles to the lines A . . . F of holes 11 and in parallel to the columns a . . . j formed by the holes 11 in adjacent lines. Each of the six slits 12 are associated to a respective section 8. In this manner definite holes 11 in adjacent sections 8 of the unit 9 are operatively connected via the slits 12 to the light-detectors 6.

The detector unit 5 is connected via not visible lines to an electronic evaluation unit 13 which comprises a plurality of evaluation channels. Light cables 41 not required for a definite sample material analysis are kept in reverse in a plug-in unit store 14. The parallel arrangement of two lines of plug-in holes 11 (for example AB, CD, EF) in a respective one of the sections 8 permits to increase the intensity of the spectral light originating from an element to be analyzed. So, for example, a further light cable 4 is inserted into an adjacent plug-in hole 11 of the neighboring line. The further light cable 4, of course, is then associated to a spectral line of the same element to be analyzed.

The edge-portion of the plug-in unit 9 is provided with position indicators 15 to identify which of the five columns f . . . j and a . . . e, respectively, is operatively connected to the underneath photocells 6 via the slits 12.

The position indicator 15 consist either of reflecting code marks which are sampled by respectively arranged signal detectors 16, or of slits. In the latter case a (not visible) light source is arranged adjacent the bottom face of the plug-in unit 9 to illuminate the code marks (15).

The radiation beam 17 originates from a radiation source 21 which is an ICP (inductively coupled plasma) in a discharge tube 22 which, in turnn, is surrounded by an induction coil or winding 23. A carrier gas tube 24 opens into the interior of the discharge tube 22.

A high frequency generator 25 supplies via lines 25' the induction coil 23 with the electrical energy required and is connected via a line 26' to a power control unit 26.

A measuring value pick-up unit 27 is connected to the high frequency generator 25 via a line 27' for detecting the electrical energy produced.

The radiation beam 17 is directed upon a deviating reflector 20 and from there upon a concave reflector 19 which is variable in its position by an adjustment means 18, the latter is connected to a position sampling means 28 which detects the actual position of the concave reflector 19 relative to the radiation source 21. A carrier gas container 30 is connected via the duct 24 to the radiation source 21. A valve 29 is inserted into the duct 24, the former is operated by a setting means 31 which for example, is a magnetic setting valve or, alternatively, a step-motor. A nebulizer 33 is inserted into the duct 24 subsequent a to the valve 29. The former has a sample input 33'. The servo-motor 10 via a line 101, the signal detector 16 via a line 16', the pick-up unit 27 via a line 27", the setting means 18 and 31, the power control unit 26 via a line 26", and the position sampling means 28 are connected to a microprocessor 32. The detector 16 detects the position of the plug-in unit 9 and in particular, of the plug-in holes 11 relative to the light detectors 6 by scanning the code marks 25. The resulting signal is fed via the line 16' into the microprocessor 32, in which the measuring parameters observation height, power efficiency, and carrier gas stream are stored for each position of the plug-in unit 9 relative to the detectors 6.

The light cables 4 which have to transmit the spectral lines which, in turn, require equal or similar measuring parameters are inserted into the plug-in holes 11 which are optically connected to the detectors 6.

After having sampled the actual values for the position of the concave reflector 19 which are indicative of the observation height and for the electrical power produced by the high frequency generator 25 the microprocessor 32 delivers a respective order to the drive 18 and to the power control unit 31 for adjustment of the measuring parameters in accordance with the set position of the plug-in unit 9. Furthermore, the drive 31 for actuating the valve 29 gets an order so that a required carrier gas flows in the duct 24 and carries a sample material to be analyzed to the radiation source. The arrangement according to the invention is not restricted to a particular optical means for dispersion. It can be used in arrangements according to Czerny-Turner, Ebert-Fasti and Rowland, as well as in echelle systems. Furthermore, the invention is not restricted to the emission spectral analysis, it can also be used in a multi-channel atom absorption analyse or in the spectral photometry.

In operation, a sample material to be analyzed is inserted via the sample input 33' into the nebulizer 33 where the sample is converted into vapor cloud which is carried via the duct 24 into the radiation source 21. The parameter locus of the sample material vapor in the source (observation height) is adjusted via the pressure of the carrier gas from the container 30, the pressure, in turn, is set by the drive 31 for the valve 29. In the radiation source 21, the elements contained in the sample material are excited at different loci of the radiation source to emit the radiation 17.

For example, the elements Na, K, Li, Pb, etc. will be excited in a first locus, more centrally in the source Fe, Ni, Cr, Co are excited to radiation, and in a third locus, P, As, C etc. are excited.

The emitted radiation 17 is directed by the reflector 20 to the concave reflector 19 which is adjusted to the respective locus, in the present embodiment to the Fe, Ni, Cr, Co - locus. The respective setting values are stored in the microprocessor 32 and via a not shown manual input the operator sets the reflector 19 via the means 18 and 28 to the central locus. The reflector 19 directs the radiation 17 upon the dispersing means 1 where depending upon the elements contained in the sample material respective spectral lines are produced. The mask 2 is provided with the respectively located slits which are in oposition to the light entry face 4' of the light cables 4 secured to the mount 3. According to the program of analyse the operator has selected the light-cables 4 each of which is associated to a respective spectral line of an element and is labeled in the most simple case by a tag (not shown). Assuming that among other elements Fe has to be detected, the light exit faces 4" are inserted into the plug-in holes 11, namely, into the hole C, for a first Fe line, and into the hole D, a for a second Fe line in the respective section 8 of the plug-in unit 9.

Of course, further light-cables 4 can be inserted into the other holes 11 for the detection of further elements. By, for example, push-button operation the servo-motor 10 starts operation and displaces according to an order signal from the microprocessor 32 via line 101 the plug-in unit 9 as long until the slits 12 lie under the columns a and f, respectively, which position is detected by the position detection unit 15, 16; when the position is arrived at the detector unit 15 delivers a respective signal via line 16' to the microprocessor 32 which delivers a stop signal to the servo-motor 10.

The light cables 4 inserted into the column a and f which transmit the spectral lines, if any, from the dispersing means 1 to the detectors 6, in the present embodiment five further elements can be sampled in addition to the two Fe spectral lines. In the same manner, the next columns b, g up to e, j are scanned by the detectors 6 which are connected to an electronic evoluation unit 13.

Hence, the detector 6 underneath the first section 8(A, B, a, b, c, d, e) receives the light from the Fe light-cables 4 and converts the light into electrical signals. These are evaluated by the electronic unit 13 and either stored by respective means (not shown) or fed into an output unit (not shown) for, for example, visual output.

A preferable embodiment would include 140 light cables 4 cemented into the mount 3, via their end-portions, and the plug-in unit 9 is conceived for an evaluation of, for example, sixty spectral lines.

The evaluation parameters namely, the observation height (locus for the excitation of definite chemical elements in the radiation source), as well as the gas-pressure and the electric power can be set at any suitable point of time of the analysing procedure, and is controlled by a respective program stored in the microprocessor 32.

The operating parameters and their interrelation are not explained in detail, they are known, for example, from ICP Information News letter, Vol. 8, No. 2, pg. 88 ff. (July 1982).

Furthermore, it has to be stated that the drawing is a very schematical outline of a spectrometer arrangement so, for example, the dispersing means 1 can have any suitable other shape, the distances between the dispersing means and the mask 2 is a matter of choice, if any. The servo-motor 10 can be substituted by a stepping-motor. In this event the detector 16 can be omitted since the stepping rate is then stored in the microprocessor 32. However, a zero-position indicator is required.

We claim:

1. A spectrometer arrangement for simultaneous analyse of a plurality of chemical elements comprising an excitation source for exciting a sample material to emit a radiation, reflector means, an optical dispersing means, said reflector means being for directing said radiation upon said optical dispersing means, said optical dispersing means producing a plurality of spectral lines in dependence of the sample material to be analyzed in a first plane, a first optical mask being associated with said optical dispersing means in a second plane and including as many exit slits in said second plane as there are spectral lines, said first plane and said second plane being substantially coincident, a plurality of light cables having each a light entry face and a light exit face, a means for mounting the light entry faces of said light cables in a third plane, said third plane being in narrow spaced and parallel relation to said second plane subsequent to said second plane, said light entry faces being optically connected via said slits to a respective one of said spectral lines, if any, a plug-in unit being provided with a plurality of plug-in holes for insertion of the light-exit faces of said light cables, said plug-in unit being subdivided into a plurality of sections of substantially equal size, a second mask being arranged subsequent to said plug-in unit at a narrow distance to the latter, said plug-in holes in said plug-in unit being substantially arranged in lines and columns being at right angles to one another, said second mask including as many slits as there are sections in said plug-in unit, said slits being aligned in parallel to said columns of plug-in holes and an right angles to said lines, each slit being associated to a respective section of said plug-in unit, an array of photodetectors being constituted of as many photo-detectors as there are sections in said plug-in unit, said array of photodetectors being arranged in a parallel plane subsequent to said second mask at a narrow space to the latter, said light exit faces of said light cables being optically connected via said plug-in unit and said second mask to respective photodetectors of said array of photodetectors, means for displacing said plug-in unit in a fourth plane defnded by said lines and columns and in directions right angles to said columns, detection means for identifying the position of a column of plug-in holes relative to the photodetectors, said detection means being provided at the edge portion of said plug-in unit adjacent said columns, a microprocessor, a first connection means for connecting said displacement means to said microprocessor, a second connection means for connecting said detection means to said microprocessor, an evaluation unit being connected to the photodetector outputs, said evaluation unit serving for evaluating the photodetector output signals, if any, indicative of a chemical matter contained in said sample material, excitation parameter adjustment means, being operatively connected to the excitation source and to said microprocessor, said microprocessor setting at least one excitation parameter on information from said detection means for a respective column of plug-in holes relative to the photodetectors.

2. An arrangement as claimed in claim 1, wherein said excitation parameter adjustment means comprise a power control unit for control of the energizing supply from a power source to a heating means for said excitation source, an adjustment means for adjusting said reflector means relative to the locus of excitation of a respective sample material in said excitation source, a control unit for controlling a carrier gas flow from a carrier gas source to said excitation source.

3. An arrangement as claimed in claim 2, wherein a sample input is provided between said control unit and said excitation source for sample material supply to the latter.

4. An arrangement as claimed in claim 3, wherein at least one line of plug-in holes is provided in each section of said plug-in unit.

5. An arrangement as claimed in claim 4, wherein each light cable, when inserted into a definite plug-in hole, serves for detecting a definite spectral line.

6. An arrangement as claimed in claim 5, wherein at least one of the adjustable parameters, namely, locus of excitation in said excitation source, power input from the power source to the heating means, and carrier gas flow, is associated with a definite spectral line and, hence, to a respective light cable insertion into a respective plug-in hole of said plug-in unit and wherein the association is stored in said microprocessor and, when said identification means delivers a respective association signal of a definite spectral line via a respective light-cable to a respective photodetector said microprocessor delivers respective setting signals to said adjustment means, and to said power control unit, and to said control unit, respectively.

7. An arrangement as claimed in claim 2, wherein light cable insertions into plug-in holes in a same column of a same section serve to increase the light intensity from different spectral lines from one chemical element.

* * * * *